(12) United States Patent  
Makin et al.

(10) Patent No.: US 7,951,095 B2  
(45) Date of Patent: May 31, 2011

(54) ULTRASOUND MEDICAL SYSTEM

(75) Inventors: Inder Raj S. Makin, Loveland, OH (US); T. Douglas Mast, Cincinnati, OH (US); Michael H. Slayton, Tempe, AZ (US); Peter G. Barthe, Phoenix, AZ (US); Jeffrey D. Messerly, Cincinnati, OH (US); Waseem Faidi, Clifton Park, NY (US); Megan M. Runk, Cincinnati, OH (US); Paul M. Jaeger, Mesa, AZ (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1928 days.

(21) Appl. No.: 10/850,038

(22) Filed: May 20, 2004

(65) Prior Publication Data

US 2005/0261585 A1    Nov. 24, 2005

(51) Int. Cl.  
*A61N 7/02* (2006.01)

(52) U.S. Cl. ............................................ 601/3; 600/549

(58) Field of Classification Search .................. 600/437, 600/438, 442, 459, 439, 472, 407, 457, 470; 607/2, 3, 6; 601/2, 3  
See application file for complete search history.

(56) References Cited

U.S. PATENT DOCUMENTS

| | | |
|---|---|---|
| 3,168,659 A | 2/1965 | Bayre et al. |
| 3,902,501 A | 9/1975 | Citron et al. |
| 3,927,557 A | 12/1975 | Viertl |
| 4,315,514 A | 2/1982 | Drewes et al. |
| 4,323,077 A | 4/1982 | Smith |
| 4,396,019 A | 8/1983 | Perry, Jr. |
| 4,484,569 A | 11/1984 | Driller et al. |
| 4,646,756 A | 3/1987 | Watnough et al. |
| 4,748,985 A | 6/1988 | Nagasaki |
| 4,757,820 A | 7/1988 | Itoh |
| 4,765,331 A | 8/1988 | Petruzzi et al. |
| 4,787,394 A | 11/1988 | Ogura |
| 4,798,215 A | 1/1989 | Turner |
| 4,818,954 A | 4/1989 | Flachenecker et al. |
| 4,844,080 A | 7/1989 | Frass et al. |
| 4,858,613 A | 8/1989 | Fry et al. |
| 4,932,414 A | 6/1990 | Coleman et al. |
| 4,937,767 A | 6/1990 | Reuschel et al. |
| 4,951,653 A | 8/1990 | Fry et al. |
| 4,955,365 A | 9/1990 | Fry et al. |
| 4,955,366 A | 9/1990 | Uchiyama et al. |

(Continued)

FOREIGN PATENT DOCUMENTS

CN    1628615    6/2005

(Continued)

OTHER PUBLICATIONS

Chavrier et al., "Modeling of high-intensity focused ultrasound-induced lesions in the presence of cavitation bubbles," J. Acoust. Soc. Am. 108 (1), pp. 432-440 (Jul. 2000).

(Continued)

*Primary Examiner* — Eric F Winakur  
*Assistant Examiner* — Vani Gupta (57) ABSTRACT

An ultrasound medical system includes an ultrasound end effector and at least one non-ultrasound tissue-property-measuring sensor. The ultrasound end effector includes a medical ultrasound transducer assembly having at least one medical-treatment ultrasound transducer. The at-least-one non-ultrasound tissue-property-measuring sensor is supported by the ultrasound end effector and is positionable in contact with patient tissue.

13 Claims, 6 Drawing Sheets

U.S. PATENT DOCUMENTS

| | | | |
|---|---|---|---|
| 4,960,107 A | 10/1990 | Aida et al. | |
| 4,960,109 A * | 10/1990 | Lele | 600/549 |
| 4,984,575 A | 1/1991 | Uchiyama et al. | |
| 4,986,275 A | 1/1991 | Ishida et al. | |
| RE33,590 E | 5/1991 | Dory | |
| 5,015,929 A | 5/1991 | Cathignol et al. | |
| 5,036,855 A | 8/1991 | Fry et al. | |
| 5,054,470 A | 10/1991 | Fry et al. | |
| 5,065,740 A | 11/1991 | Itoh | |
| 5,078,144 A | 1/1992 | Sekino et al. | |
| 5,080,101 A | 1/1992 | Dory | |
| 5,080,102 A | 1/1992 | Dory | |
| 5,095,907 A | 3/1992 | Kudo et al. | |
| 5,117,832 A | 6/1992 | Sanghvi et al. | |
| 5,143,073 A | 9/1992 | Dory | |
| 5,143,074 A | 9/1992 | Dory | |
| 5,149,319 A | 9/1992 | Unger | |
| 5,150,711 A | 9/1992 | Dory | |
| 5,150,712 A | 9/1992 | Dory | |
| 5,158,070 A | 10/1992 | Dory | |
| 5,158,071 A | 10/1992 | Umemura et al. | |
| 5,203,333 A | 4/1993 | Nomura | |
| 5,209,221 A | 5/1993 | Riedlinger | |
| 5,238,007 A | 8/1993 | Giele et al. | |
| 5,240,005 A | 8/1993 | Viebach | |
| 5,242,437 A | 9/1993 | Everett et al. | |
| 5,295,484 A | 3/1994 | Marcus et al. | |
| 5,304,115 A | 4/1994 | Pflueger et al. | |
| 5,305,731 A | 4/1994 | Buchholtz | |
| 5,311,869 A | 5/1994 | Okazaki | |
| 5,348,017 A * | 9/1994 | Thornton et al. | 600/467 |
| 5,354,258 A | 10/1994 | Dory | |
| 5,391,140 A | 2/1995 | Schaetzle et al. | |
| 5,391,197 A | 2/1995 | Burdette et al. | |
| 5,402,792 A | 4/1995 | Kimura | |
| 5,409,002 A | 4/1995 | Pell | |
| 5,413,550 A | 5/1995 | Castel | |
| 5,419,335 A | 5/1995 | Hartmann et al. | |
| 5,431,663 A | 7/1995 | Carter | |
| 5,435,304 A | 7/1995 | Oppelt et al. | |
| 5,435,311 A | 7/1995 | Umemura et al. | |
| 5,443,069 A | 8/1995 | Schaetzle | |
| 5,448,994 A | 9/1995 | Iinuma | |
| 5,458,597 A | 10/1995 | Edwards et al. | |
| 5,465,724 A | 11/1995 | Sliwa et al. | |
| 5,471,988 A | 12/1995 | Fujio et al. | |
| 5,474,071 A | 12/1995 | Chapelon et al. | |
| 5,485,839 A | 1/1996 | Aida et al. | |
| 5,492,126 A | 2/1996 | Hennige et al. | |
| 5,500,012 A | 3/1996 | Brucker et al. | |
| 5,501,655 A | 3/1996 | Rolt et al. | |
| 5,514,085 A | 5/1996 | Yoon | |
| 5,514,130 A | 5/1996 | Baker | |
| 5,520,188 A | 5/1996 | Hennige et al. | |
| 5,522,869 A | 6/1996 | Burdette et al. | |
| 5,524,620 A | 6/1996 | Rosenschein | |
| 5,526,815 A | 6/1996 | Granz et al. | |
| 5,526,822 A | 6/1996 | Burbank et al. | |
| 5,540,656 A | 7/1996 | Pflueger et al. | |
| 5,545,195 A | 8/1996 | Lennox et al. | |
| 5,547,459 A | 8/1996 | Kaufman et al. | |
| 5,549,638 A | 8/1996 | Burdette | |
| 5,558,092 A | 9/1996 | Unger et al. | |
| 5,569,241 A | 10/1996 | Edwards | |
| 5,571,088 A | 11/1996 | Lennox et al. | |
| 5,573,497 A | 11/1996 | Chapelon | |
| 5,575,288 A | 11/1996 | Sliwa et al. | |
| 5,575,772 A | 11/1996 | Lennox | |
| 5,575,789 A | 11/1996 | Bell et al. | |
| 5,582,588 A | 12/1996 | Sakurai et al. | |
| 5,588,432 A * | 12/1996 | Crowley | 600/439 |
| 5,590,657 A | 1/1997 | Cain et al. | |
| 5,601,526 A | 2/1997 | Chapelon et al. | |
| 5,620,479 A | 4/1997 | Diederich | |
| 5,624,382 A | 4/1997 | Oppelt et al. | |
| 5,628,743 A | 5/1997 | Cimino | |
| 5,630,837 A | 5/1997 | Crowley | |
| 5,643,179 A | 7/1997 | Fujimoto | |
| 5,649,547 A | 7/1997 | Ritchart et al. | |
| 5,657,760 A | 8/1997 | Ying et al. | |
| 5,665,054 A | 9/1997 | Dory | |
| 5,666,954 A | 9/1997 | Chapelon et al. | |
| 5,676,692 A | 10/1997 | Sanghvi et al. | |
| 5,687,729 A | 11/1997 | Schaetzle | |
| 5,694,936 A | 12/1997 | Fujimoto et al. | |
| 5,697,897 A | 12/1997 | Buchholtz et al. | |
| 5,699,804 A | 12/1997 | Rattner | |
| 5,703,922 A | 12/1997 | Rattner | |
| 5,715,825 A | 2/1998 | Crowley | |
| 5,720,287 A | 2/1998 | Chapelon et al. | |
| 5,722,411 A | 3/1998 | Suzuki et al. | |
| 5,728,062 A | 3/1998 | Brisken | |
| 5,733,315 A | 3/1998 | Burdette et al. | |
| 5,735,280 A | 4/1998 | Sherman et al. | |
| 5,735,796 A | 4/1998 | Granz et al. | |
| 5,738,635 A | 4/1998 | Chapelon et al. | |
| 5,743,862 A | 4/1998 | Izumi | |
| 5,743,863 A | 4/1998 | Chapelon | |
| 5,746,224 A | 5/1998 | Edwards | |
| 5,759,154 A | 6/1998 | Hoyns | |
| 5,759,162 A | 6/1998 | Oppelt et al. | |
| 5,762,066 A | 6/1998 | Law et al. | |
| 5,769,086 A | 6/1998 | Ritchart et al. | |
| 5,769,790 A | 6/1998 | Watkins et al. | |
| 5,771,896 A | 6/1998 | Sliwa et al. | |
| 5,785,705 A | 7/1998 | Baker | |
| 5,788,636 A | 8/1998 | Curley | |
| 5,800,379 A | 9/1998 | Edwards | |
| 5,800,429 A | 9/1998 | Edwards | |
| 5,807,308 A | 9/1998 | Edwards | |
| 5,817,021 A | 10/1998 | Reichenberger | |
| 5,817,049 A | 10/1998 | Edwards | |
| 5,820,580 A | 10/1998 | Edwards et al. | |
| 5,823,962 A | 10/1998 | Schaetzle et al. | |
| 5,836,896 A | 11/1998 | Rosenschein | |
| 5,840,031 A | 11/1998 | Crowley | |
| 5,842,994 A | 12/1998 | TenHoff et al. | |
| 5,860,974 A | 1/1999 | Abele | |
| 5,873,828 A | 2/1999 | Fujio et al. | |
| 5,873,845 A | 2/1999 | Cline et al. | |
| 5,873,902 A | 2/1999 | Sanghvi et al. | |
| 5,876,399 A | 3/1999 | Chia et al. | |
| 5,882,302 A | 3/1999 | Driscoll, Jr. et al. | |
| 5,895,356 A | 4/1999 | Andrus et al. | |
| 5,897,495 A | 4/1999 | Aida et al. | |
| 5,897,523 A | 4/1999 | Wright et al. | |
| 5,925,044 A | 7/1999 | Hofmann et al. | |
| 5,928,169 A | 7/1999 | Schatzle et al. | |
| 5,931,848 A | 8/1999 | Saadat | |
| 5,938,600 A | 8/1999 | Van Vaals et al. | |
| 5,938,608 A | 8/1999 | Bieger et al. | |
| 5,938,659 A | 8/1999 | Tu et al. | |
| 5,944,663 A | 8/1999 | Kuth et al. | |
| 5,964,755 A | 10/1999 | Edwards | |
| 5,979,453 A | 11/1999 | Savage et al. | |
| 5,984,881 A | 11/1999 | Ishibashi et al. | |
| 5,984,882 A | 11/1999 | Rosenschein et al. | |
| 5,993,389 A | 11/1999 | Driscoll, Jr. et al. | |
| 5,997,534 A | 12/1999 | Tu et al. | |
| 6,001,069 A | 12/1999 | Tachibana et al. | |
| 6,004,269 A | 12/1999 | Crowley et al. | |
| 6,007,499 A | 12/1999 | Martin et al. | |
| 6,022,319 A | 2/2000 | Willard et al. | |
| 6,024,718 A | 2/2000 | Chen et al. | |
| 6,024,740 A | 2/2000 | Lesh et al. | |
| 6,027,449 A | 2/2000 | Mazess et al. | |
| 6,033,397 A | 3/2000 | Laufer et al. | |
| 6,039,689 A | 3/2000 | Lizzi | |
| 6,041,260 A * | 3/2000 | Stern et al. | 607/98 |
| 6,042,556 A | 3/2000 | Beach et al. | |
| 6,050,943 A | 4/2000 | Slayton et al. | |
| 6,066,123 A | 5/2000 | Li et al. | |
| 6,071,238 A | 6/2000 | Chapelon et al. | |
| 6,071,239 A | 6/2000 | Cribbs et al. | |
| 6,083,159 A | 7/2000 | Driscoll, Jr. et al. | |
| 6,086,535 A | 7/2000 | Ishibashi et al. | |
| 6,086,583 A | 7/2000 | Ouchi | |

| | | |
|---|---|---|
| 6,088,613 A | 7/2000 | Unger |
| 6,106,469 A | 8/2000 | Suzuki et al. |
| 6,106,517 A | 8/2000 | Zupkas |
| 6,112,123 A | 8/2000 | Kelleher et al. |
| 6,113,558 A | 9/2000 | Rosenschein et al. |
| 6,117,101 A | 9/2000 | Diederich et al. |
| 6,135,963 A | 10/2000 | Haider |
| 6,135,971 A | 10/2000 | Hutchinson et al. |
| 6,138,513 A | 10/2000 | Barabash et al. |
| 6,148,224 A | 11/2000 | Jensen |
| 6,156,029 A | 12/2000 | Mueller |
| 6,171,248 B1 | 1/2001 | Hossack et al. |
| 6,176,842 B1 | 1/2001 | Tachibana et al. |
| 6,183,469 B1 | 2/2001 | Thapliyal et al. |
| 6,210,330 B1 | 4/2001 | Tepper |
| 6,216,704 B1 | 4/2001 | Ingle et al. |
| 6,217,576 B1 | 4/2001 | Tu et al. |
| 6,231,834 B1 | 5/2001 | Unger et al. |
| 6,352,532 B1 | 3/2002 | Kramer et al. |
| 6,361,531 B1 | 3/2002 | Hissong |
| 6,371,903 B1 | 4/2002 | Blanc et al. |
| 6,379,320 B1 | 4/2002 | Lafon et al. |
| 6,394,949 B1 | 5/2002 | Crowley et al. |
| 6,425,867 B1 | 7/2002 | Vaezy et al. |
| 6,482,178 B1 | 11/2002 | Andrews et al. |
| 6,508,774 B1 | 1/2003 | Acker et al. |
| 6,512,957 B1 | 1/2003 | Witte |
| 6,521,211 B1 | 2/2003 | Unger et al. |
| 6,533,726 B1 | 3/2003 | Lizzi et al. |
| 6,546,934 B1 | 4/2003 | Ingle et al. |
| 6,547,788 B1 * | 4/2003 | Maguire et al. .......... 606/41 |
| 6,575,956 B1 | 6/2003 | Brisken et al. |
| 6,599,245 B1 | 7/2003 | Ma et al. |
| 6,602,251 B2 | 8/2003 | Burbank et al. |
| 6,613,004 B1 | 9/2003 | Vitek et al. |
| 6,618,620 B1 | 9/2003 | Freundlich et al. |
| 6,626,855 B1 | 9/2003 | Weng et al. |
| 6,645,202 B1 | 11/2003 | Pless et al. |
| 6,669,638 B1 | 12/2003 | Miller et al. |
| 6,716,184 B2 | 4/2004 | Vaezy et al. |
| 6,719,694 B2 | 4/2004 | Weng et al. |
| 6,740,082 B2 | 5/2004 | Shadduck |
| 6,764,488 B1 | 7/2004 | Burbank et al. |
| 6,770,070 B1 | 8/2004 | Balbierz |
| 6,783,524 B2 * | 8/2004 | Anderson et al. .......... 606/28 |
| 6,887,239 B2 | 5/2005 | Elstrom et al. |
| 6,902,536 B2 | 6/2005 | Manna et al. |
| 6,921,371 B2 | 7/2005 | Wilson |
| 6,936,024 B1 | 8/2005 | Houser |
| 6,936,048 B2 | 8/2005 | Hurst |
| 6,974,417 B2 | 12/2005 | Lockwood et al. |
| 7,037,306 B2 | 5/2006 | Podany et al. |
| 7,063,666 B2 | 6/2006 | Weng et al. |
| 7,078,015 B2 | 7/2006 | Unger |
| 7,247,141 B2 | 7/2007 | Makin et al. |
| 7,473,250 B2 | 1/2009 | Makin et al. |
| 7,494,467 B2 | 2/2009 | Makin et al. |
| 7,695,436 B2 | 4/2010 | Mast et al. |
| 2001/0007940 A1 | 7/2001 | Tu et al. |
| 2001/0014805 A1 | 8/2001 | Burbank et al. |
| 2001/0037073 A1 | 11/2001 | White et al. |
| 2002/0065512 A1 | 5/2002 | Fjield et al. |
| 2002/0068934 A1 | 6/2002 | Edwards et al. |
| 2002/0072741 A1 | 6/2002 | Sliwa et al. |
| 2002/0087081 A1 | 7/2002 | Serrano et al. |
| 2002/0087083 A1 | 7/2002 | Nix et al. |
| 2002/0111662 A1 | 8/2002 | Iaizzo et al. |
| 2002/0147447 A1 | 10/2002 | Long |
| 2002/0156470 A1 | 10/2002 | Shadduck |
| 2002/0165579 A1 | 11/2002 | Burbank et al. |
| 2002/0183742 A1 | 12/2002 | Carmel et al. |
| 2002/0183771 A1 | 12/2002 | Burbank et al. |
| 2002/0193781 A1 | 12/2002 | Loeb |
| 2003/0004434 A1 | 1/2003 | Greco et al. |
| 2003/0013960 A1 | 1/2003 | Makin et al. |
| 2003/0013971 A1 | 1/2003 | Makin et al. |
| 2003/0018266 A1 | 1/2003 | Makin et al. |
| 2003/0018358 A1 * | 1/2003 | Saadat .......... 606/232 |
| 2003/0028111 A1 | 2/2003 | Vaezy et al. |
| 2003/0040698 A1 | 2/2003 | Makin et al. |
| 2003/0047582 A1 | 3/2003 | Sonnenschein et al. |
| 2003/0073907 A1 | 4/2003 | Taylor |
| 2003/0109786 A1 | 6/2003 | Irioka et al. |
| 2003/0120270 A1 | 6/2003 | Acker |
| 2003/0144593 A1 | 7/2003 | Whitmore et al. |
| 2003/0181900 A1 | 9/2003 | Long |
| 2003/0212331 A1 | 11/2003 | Fenton et al. |
| 2003/0212332 A1 | 11/2003 | Fenton et al. |
| 2003/0220568 A1 | 11/2003 | Hansmann et al. |
| 2003/0225331 A1 | 12/2003 | Diederich et al. |
| 2003/0229293 A1 | 12/2003 | Hibner et al. |
| 2003/0233091 A1 | 12/2003 | Whayne et al. |
| 2004/0006336 A1 | 1/2004 | Swanson |
| 2004/0030268 A1 | 2/2004 | Weng et al. |
| 2004/0143252 A1 | 7/2004 | Hurst |
| 2004/0236375 A1 | 11/2004 | Redding, Jr. |
| 2004/0254570 A1 | 12/2004 | Hadjicostis et al. |
| 2005/0015107 A1 | 1/2005 | O'Brien |
| 2005/0085726 A1 | 4/2005 | Lacoste et al. |
| 2005/0137520 A1 | 6/2005 | Rule et al. |
| 2005/0228286 A1 | 10/2005 | Messerly et al. |
| 2005/0234438 A1 | 10/2005 | Mast et al. |
| 2005/0240123 A1 | 10/2005 | Mast et al. |
| 2005/0240124 A1 | 10/2005 | Mast et al. |
| 2005/0240125 A1 | 10/2005 | Makin et al. |
| 2005/0256405 A1 | 11/2005 | Makin et al. |
| 2005/0261586 A1 | 11/2005 | Makin et al. |
| 2005/0261587 A1 | 11/2005 | Makin et al. |
| 2005/0261588 A1 | 11/2005 | Makin et al. |
| 2005/0267488 A1 | 12/2005 | Hare et al. |
| 2006/0052695 A1 | 3/2006 | Adam |
| 2006/0052701 A1 | 3/2006 | Carter et al. |
| 2006/0173348 A1 | 8/2006 | Wilser et al. |
| 2006/0235306 A1 | 10/2006 | Cotter et al. |
| 2007/0016184 A1 | 1/2007 | Cropper et al. |
| 2007/0021691 A1 | 1/2007 | Nita et al. |
| 2008/0058648 A1 | 3/2008 | Novak et al. |
| 2008/0287837 A1 | 11/2008 | Makin et al. |
| 2009/0198156 A1 | 8/2009 | Mast et al. |

FOREIGN PATENT DOCUMENTS

| | | |
|---|---|---|
| EP | 1518498 | 3/2005 |
| JP | 01-288242 | 11/1989 |
| JP | 06-181923 | 7/1994 |
| JP | 10-14967 | 1/1998 |
| WO | WO 01/45550 A2 | 6/2001 |

OTHER PUBLICATIONS

Watkin et al., "High-intensity focused ultrasound ablation of the kidney in a large animal model," J. Endourol., 11(3), 191, abstract (Jun. 1997).

Hill, C.R. et al., Lesion Development in Focused Ultrasound Surgery: A General Model, Ultrasound in Med. & Biol., 1994, pp. 259-269, vol. 20, No. 3, Elsevier Science Ltd, New York, USA.

Clare, M.C. et al., MRI Guided Focused Ultrasound Surgery (FUS) of uterine leiomyomas: A Feasibility Study, Workshop on MRI-Guided: Focused Ultrasound Surgery, 2002, Syllabus, International Society for Magnetic Resonance in Medicine.

Vaezy, S. et al., Treatment of Uterine Fibroid Tumors in a Nude Mouse Model Using High-Intensity Focused Ultrasound, Am J Obstet Gynecol, 2000, pp. 6-11, vol. 183, No. 1.

Cool-tip™ RF Tadio Frequency Ablation System, web page from radionics.com.

Electrosurgical Devices, RF Generator and RITA Base Software, web pages from ritamedical.com.

Billard, et al., "Effects of Physical Parameters in High Temperature Ultrasound Hyperthermia," Ultrasound in Medicine and Biology, vol. 16, Issue 4, pp. 409-420 (1990).

Office Action, Chinese Application No. 200680032059.2 (6 pages) (Nov. 6, 2009).

Supplementary European Search Report, European Application No. 06787104.6 (8 pages) (Sep. 16, 2009).

* cited by examiner

ULTRASOUND MEDICAL SYSTEM

FIELD OF THE INVENTION

The present invention relates generally to ultrasound, and more particularly to ultrasound medical systems and methods.

BACKGROUND OF THE INVENTION

Known medical methods include using ultrasound imaging (at low power) of patients to identify patient tissue for medical treatment and include using ultrasound (at high power) to ablate identified patient tissue by heating the tissue.

Known ultrasound medical systems and methods include deploying an ultrasound end effector having an ultrasound transducer outside the body to break up kidney stones inside the body, endoscopically inserting an ultrasound end effector having an ultrasound transducer in the rectum to medically destroy prostate cancer, laparoscopically inserting an ultrasound end effector having an ultrasound transducer in the abdominal cavity to medically destroy a cancerous liver tumor, intravenously inserting a catheter ultrasound end effector having an ultrasound transducer into a vein in the arm and moving the catheter to the heart to medically destroy diseased heart tissue, and interstitially inserting a needle ultrasound end effector having an ultrasound transducer needle into the tongue to medically destroy tissue to reduce tongue volume to reduce snoring.

Rotatable ultrasound end effectors are known wherein an ultrasound transducer is non-rotatably attached to a shaft whose distal end is circumferentially and longitudinally surrounded by a sheath having a longitudinal axis and having an acoustic window. Water between the shaft and the sheath provides acoustic coupling between the ultrasound transducer and the acoustic window. The shaft is rotatable about the longitudinal axis with respect to the sheath. The sheath is non-rotatably attached to a handpiece.

Known medical systems and methods include deploying a radio-frequency (RF) end effector having an RF electrode to thermally ablate patient tissue and to take tissue electric impedance and tissue temperature measurements using electrodes integrated into the shaft or into a tine which also helps stabilize the RF end effector in patient tissue.

Still, scientists and engineers continue to seek improved ultrasound medical systems and methods.

SUMMARY OF THE INVENTION

An embodiment of the invention is an ultrasound medical system including an ultrasound end effector and including at least one non-ultrasound tissue-property-measuring sensor. The ultrasound end effector includes a medical ultrasound transducer assembly having at least one medical-treatment ultrasound transducer. The at-least-one non-ultrasound tissue-property-measuring sensor is supported by the ultrasound end effector and is positionable in contact with patient tissue.

Several benefits and advantages are obtained from one or more of the embodiments and methods of the invention. In one example, having a non-ultrasound tissue-property-measuring sensor (such as a tissue temperature sensor and/or a tissue electric impedance sensor) allows ultrasound tissue ablation with feedback from the sensor used to evaluate the tissue ablation and/or modify the ultrasound treatment.

The present invention has, without limitation, application in conventional interstitial, endoscopic, laparoscopic, and open surgical instrumentation as well as application in robotic-assisted surgery.

DETAILED DESCRIPTION OF THE INVENTION

Before explaining the present invention in detail, it should be noted that the invention is not limited in its application or use to the details of construction and arrangement of parts and/or steps illustrated in the accompanying drawings and description. The illustrative embodiments and methods of the invention may be implemented or incorporated in other embodiments, methods, variations and modifications, and may be practiced or carried out in various ways. Furthermore, unless otherwise indicated, the terms and expressions employed herein have been chosen for the purpose of describing the illustrative embodiments and methods of the present invention for the convenience of the reader and are not for the purpose of limiting the invention.

It is understood that any one or more of the following-described embodiments, methods, examples, etc. can be combined with any one or more of the other following-described embodiments, methods, examples, etc.

Figure 1:
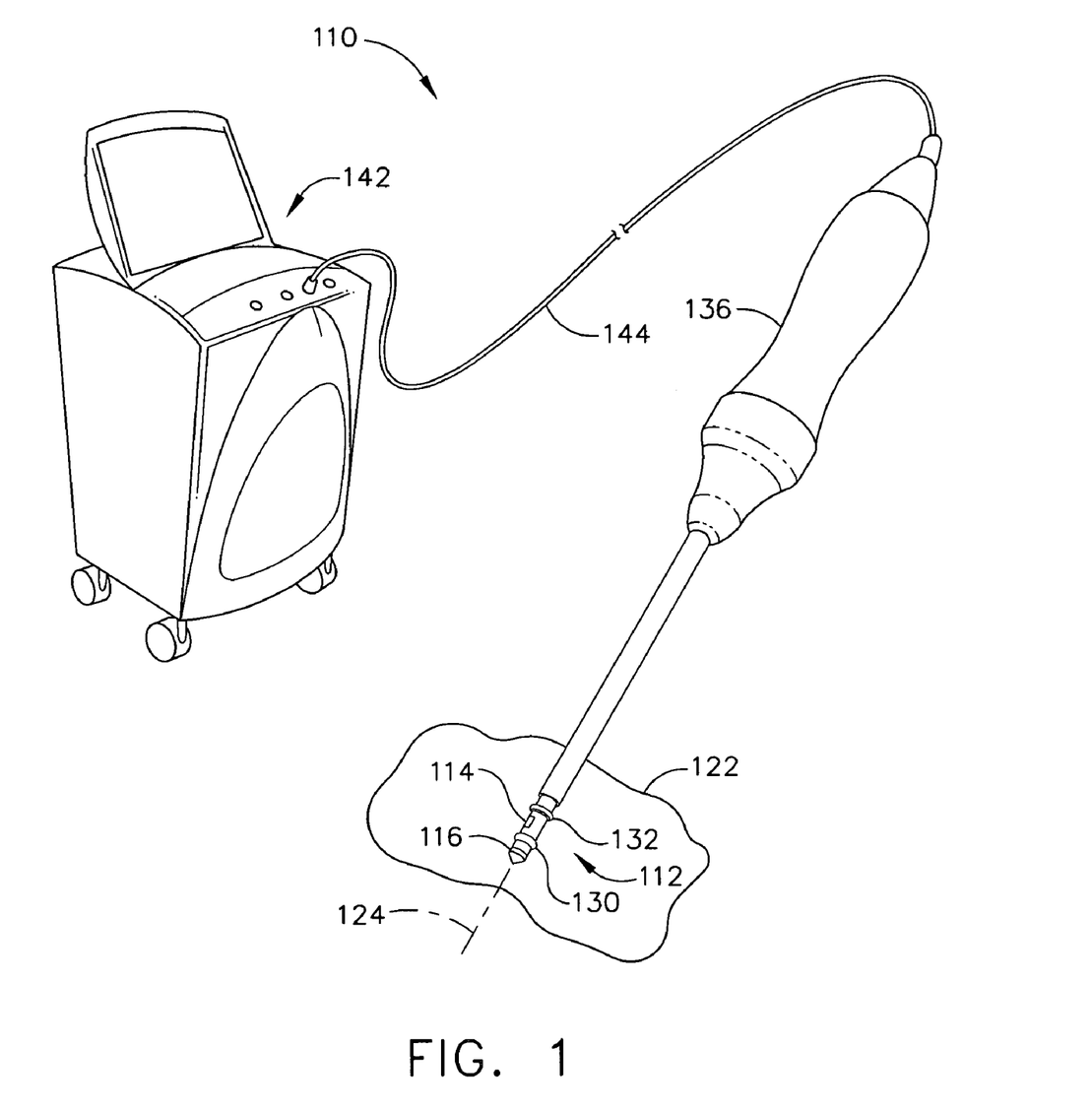
FIG. 1 is a perspective view of a first embodiment of the present invention showing an ultrasound medical system which includes an end effector, a handpiece, and a controller.
Figure 2:
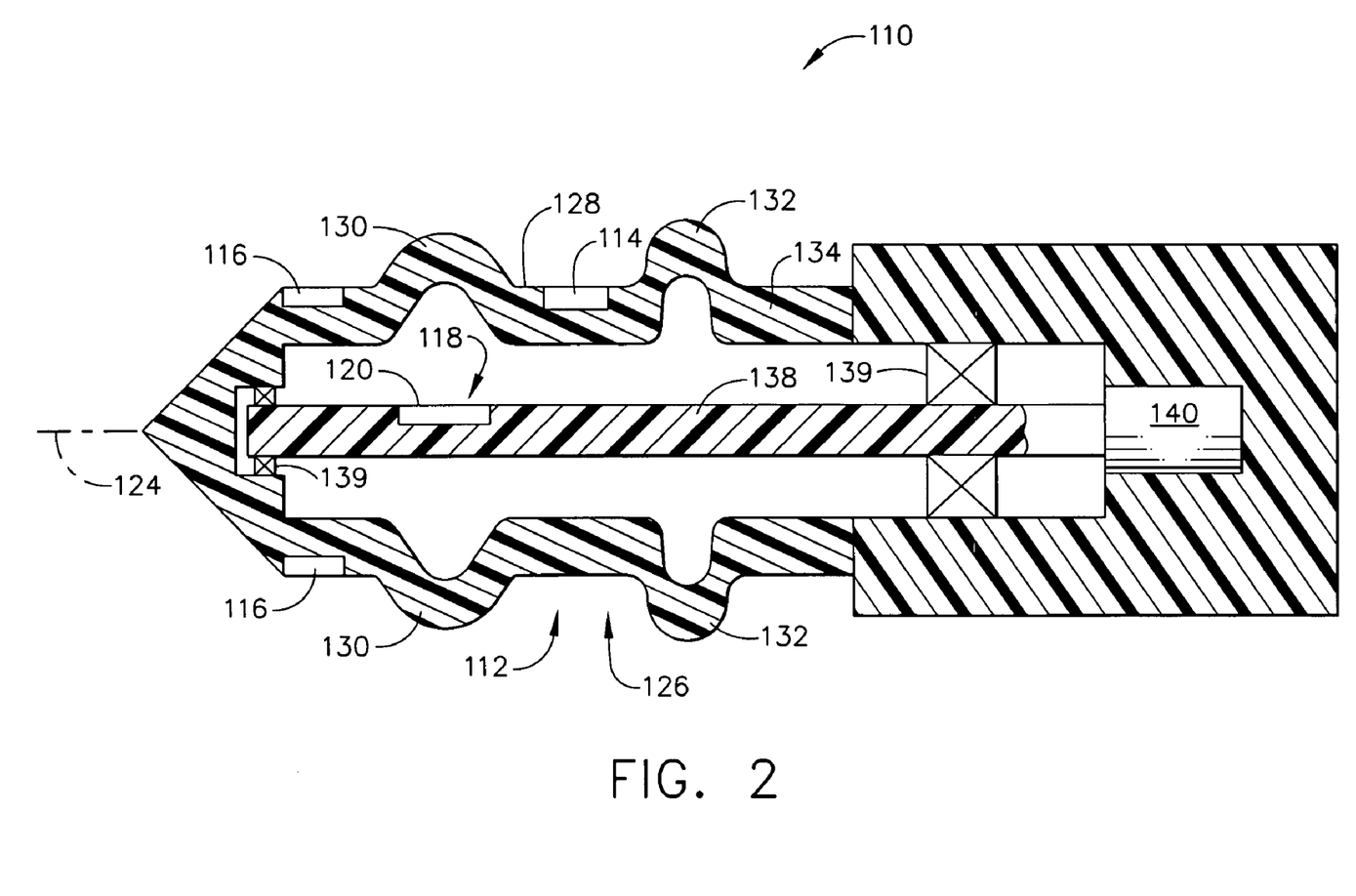
FIG. 2 is a schematic cross-sectional view of a first embodiment of the end effector and the handpiece of the ultrasound medical system of FIG. 1 showing a medical ultrasound transducer assembly and two non-ultrasound tissue-property-measuring sensors.

Referring now to FIGS. 1-2 of the drawings, a first embodiment of the present invention is an ultrasound medical system 110 comprising an ultrasound end effector 112 and at least one non-ultrasound tissue-property-measuring sensor 114 and 116. The ultrasound end effector 112 includes a medical ultrasound transducer assembly 118 having at least one medical-treatment ultrasound transducer 120. The at-least-one non-ultrasound tissue-property-measuring sensor 114 and 116 is supported by the ultrasound end effector 112 and is disposable in contact with patient tissue 122.

It is noted that a medical-treatment ultrasound transducer includes a medical-treatment-only ultrasound transducer and a medical-imaging-and-treatment ultrasound transducer. In one arrangement, an ultrasound transducer has a single transducer element, and in another arrangement, an ultrasound transducer has a plurality (also called an array) of transducer elements. It is also noted that a medical ultrasound transducer assembly having at least one medical-treatment ultrasound transducer can also have at least one medical-imaging ultrasound transducer.

In one example of the embodiment of FIGS. 1-2, the ultrasound end effector 112 includes a longitudinal axis 124. In this example, the at-least-one non-ultrasound tissue-property-measuring sensor 114 and 116 includes a first non-ultrasound tissue-property-measuring sensor 114 and a second non-ultrasound tissue-property-measuring sensor 116. The at-least-one medical-treatment ultrasound transducer 120 is disposed longitudinally between the first and second non-ultrasound tissue-property-measuring sensors 114 and 116.

In one variation of the embodiment of FIGS. 1-2, the at-least-one non-ultrasound tissue-property-measuring sensor (e.g., 114) measures tissue temperature. In one modification, the at-least-one non-ultrasound tissue-property-measuring sensor (e.g., 114) is chosen from the group consisting of a thermistor, a thermocouple, and combinations thereof. In another variation, the at-least-one non-ultrasound tissue-property-measuring sensor (e.g., 116) measures tissue electric impedance. In one modification, the at-least-one non-ultrasound tissue-property-measuring sensor (e.g., 116) is chosen from the group consisting of a monopolar electrode, a bipolar electrode, and combinations thereof. It is noted that tissue temperature and/or tissue electric impedance is a measure of the degree of ultrasonic ablation of patient tissue, as can be appreciated by those skilled in the art.

In one construction of the embodiment of FIGS. 1-2, the ultrasound end effector 112 is an ultrasound interstitial end effector 126 which is interstitially insertable into patient tissue 122 and which has an exterior surface 128. The at-least-one non-ultrasound tissue-property-measuring sensor 114 and 116 is attached to the ultrasound interstitial end effector 126 and is fixedly disposed substantially flush with the exterior surface 128. In one arrangement, the exterior surface 128 includes at least one balloon portion 130 and 132 which is expandable and contractible and which is expandable against patient tissue 122 to provide at least some stabilization of the ultrasound interstitial end effector 126 with respect to patient tissue 122. In one variation, the exterior surface 128 is the exterior surface of a sheath 134 and has first and second balloon portions 130 and 132, wherein the first balloon portion 130 surrounds the medical ultrasound transducer assembly 118 and acts as an acoustic window, and wherein the second balloon portion 132 is longitudinally spaced apart from the medical ultrasound transducer assembly 118. An acoustic coupling medium, such as water, is disposable between the medical ultrasound transducer assembly 118 and the first balloon portion 130 and has been omitted from FIG. 2 for clarity. In one modification, the first balloon portion 130 is omitted and the sheath 134 terminates before the medical ultrasound transducer assembly 118 which is exposed to patient tissue. In another modification, the second balloon portion 132 is omitted. In one employment, the at-least-one balloon portion 130 and 132 is contracted during tissue insertion and withdrawal of the ultrasound interstitial end effector 126. Other constructions, arrangements, variations, and modifications are left to the artisan.

In one enablement of the embodiment of FIGS. 1-2, the ultrasound end effector 112 is an ultrasound interstitial end effector 126 which is interstitially insertable into patient tissue 122 and which has an exterior surface 128. In this enablement, the at-least-one non-ultrasound tissue-property-measuring sensor 114 and 116 is deployable to extend away from the exterior surface into patient tissue 128 to provide at least some stabilization of the ultrasound interstitial end effector 126 with respect to patient tissue 122 and is retrievable to retract back toward the exterior surface 128. In one arrangement, the at-least-one non-ultrasound tissue-property-measuring sensor 114 and 116 is storable inside the exterior surface.

In one implementation of the embodiment of FIGS. 1-2, the ultrasound medical system 110 also includes a handpiece 136 operatively connected to the ultrasound end effector 112, The ultrasound end effector 112 has a longitudinal axis 124 and a shaft 138, and the medical ultrasound transducer assembly 118 is supported by the shaft 138. The shaft 138 is rotatable with respect to the handpiece 136 about the longitudinal axis 124 and is supported by bearings 139. In one variation, a motor 140 rotates the shaft 138. In one arrangement, the ultrasound medical system 110 includes a controller 142 operatively connected to the handpiece 136 via a cable 144.

Figure 3:
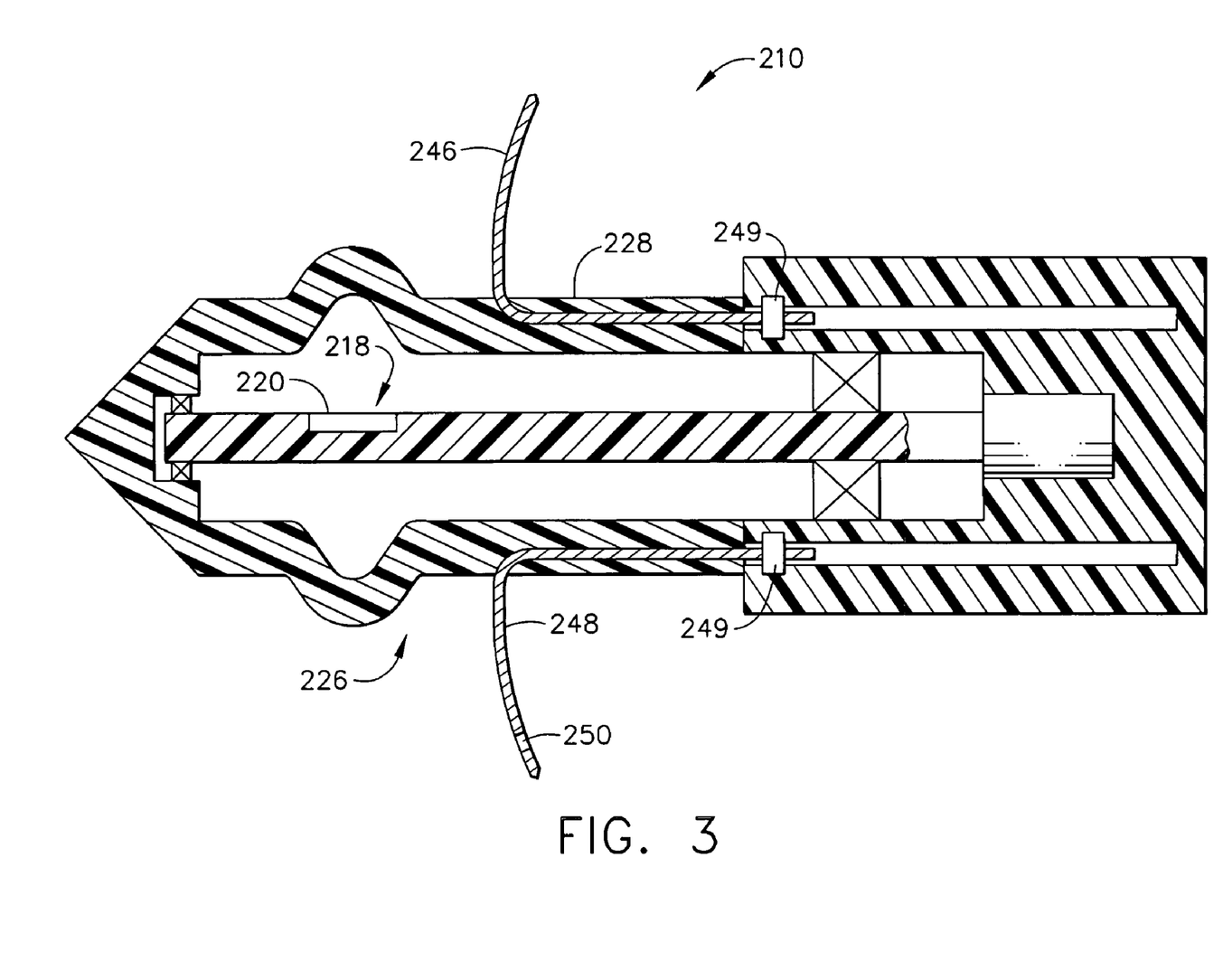
FIG. 3 is a view, as in FIG. 2, but of a second embodiment of a handpiece and of an end effector having a medical ultrasound transducer assembly and two tines.

A second embodiment of the present invention, shown in FIG. 3, is an ultrasound medical system 210 comprising an ultrasound end effector 226. The ultrasound end effector 226 has an exterior surface 228. The ultrasound end effector 226 includes a medical ultrasound transducer assembly 218 having at least one medical-treatment ultrasound transducer 220, and includes at least one tine 246 and 248. The at-least-one tine 246 and 248 is deployable to extend away from the exterior surface into patient tissue to provide at least some stabilization of the ultrasound end effector 226 with respect to patient tissue and is retrievable to retract back toward the exterior surface 228.

In one example of the embodiment of FIG. 3, the ultrasound end effector 226 is insertable into a patient. In one variation, the ultrasound end effector 226 is an ultrasound interstitial end effector which is interstitially insertable into patient tissue. In other variations, the ultrasound end effector is insertable into a patient in an endoscopic, laparoscopic, and/or open surgical manner. In another example, the ultrasound end effector is disposable on the outside of a patient. Other examples and variations are left to the artisan.

In one enablement of the embodiment of FIG. 3, the at-least-one tine 246 and 248 includes a plurality of tines. In one example of the embodiment of FIG. 3, the at-least-one tine 246 and 248 is storable inside the exterior surface. It is noted that construction of deployable tines 246 and 248 in an ultrasound end effector 226 is within the level of skill of the artisan. In one arrangement, such deployment is accomplished using one or more of cables, levers, motors 249, gearing, push rods and the like to move a tine partially out of, and back into, a lumen in the end effector. In one choice of materials, the tine comprises or consists essentially of Nitinol wire or nichrome wire.

In one employment of the embodiment of FIG. 3, the at-least-one tine (e.g., 246) acts as an element chosen from the group consisting of an electrode, a thermistor, a thermocouple, an acoustic reflector, an acoustic absorber, an acoustic emitter, an acoustic receiver, a radio-frequency (RF) heater, a resistive heater, and combinations thereof. In another employment, the at-least-one tine (e.g., 248) includes a component 250 chosen from the group consisting of an electrode, a thermistor, a thermocouple, an acoustic reflector, an acoustic absorber, an acoustic emitter, an acoustic receiver, a radio-frequency (RF) heater, a resistive heater, and combinations thereof.

The embodiment, examples, constructions, implementations, etc. of the embodiment of FIGS. 1-2 are equally applicable to the embodiment, constructions, implementations, etc. of FIG. 3. In one construction of the embodiment of FIG. 3, the exterior surface 228 is like the exterior surface 128 of a previously-illustrated and described construction of the embodiment of FIGS. 1-2 including at least one balloon portion which is expandable and contractible, and which is expandable against patient tissue to provide at least some stabilization of the ultrasound end effector with respect to patient tissue. In one implementation of the embodiment of FIG. 3, the ultrasound medical system 210 also includes, like a previously-illustrated and described implementation of the embodiment of FIGS. 1-2, a handpiece operatively connected to the ultrasound end effector, wherein the ultrasound end effector has a longitudinal axis and a shaft, wherein the medical ultrasound transducer assembly is supported by the shaft, and wherein the shaft is rotatable with respect to the handpiece about the longitudinal axis.

One method, using the embodiment of FIG. 3 and enablements, examples, employments, and constructions thereof, is for ultrasonically treating a lesion in a patient and includes steps a) through f). Step a) includes obtaining the ultrasound medical system 210. Step b) includes inserting the ultrasound end effector 226 into patient tissue. Step c) includes deploying the plurality of tines 246 and 248 to extend sway from the exterior surface 228 into the patient tissue. Step d) includes ultrasonically ablating the lesion using the at-least-one medical-treatment ultrasound transducer 220. Step e) includes retrieving the plurality of tines 246 and 248 to retract back toward the exterior surface and storing the plurality of tines 246 and 248 inside the exterior surface 228. Step f) includes withdrawing the ultrasound end effector 226 from the patient tissue. Another method also includes the step of employing the plurality of tines 246 and 248 to each act as the element or using each component 250. An additional method also includes the step of expanding the at-least-one balloon portion against patient tissue and contracting the at-least-one balloon portion.

Figure 4:
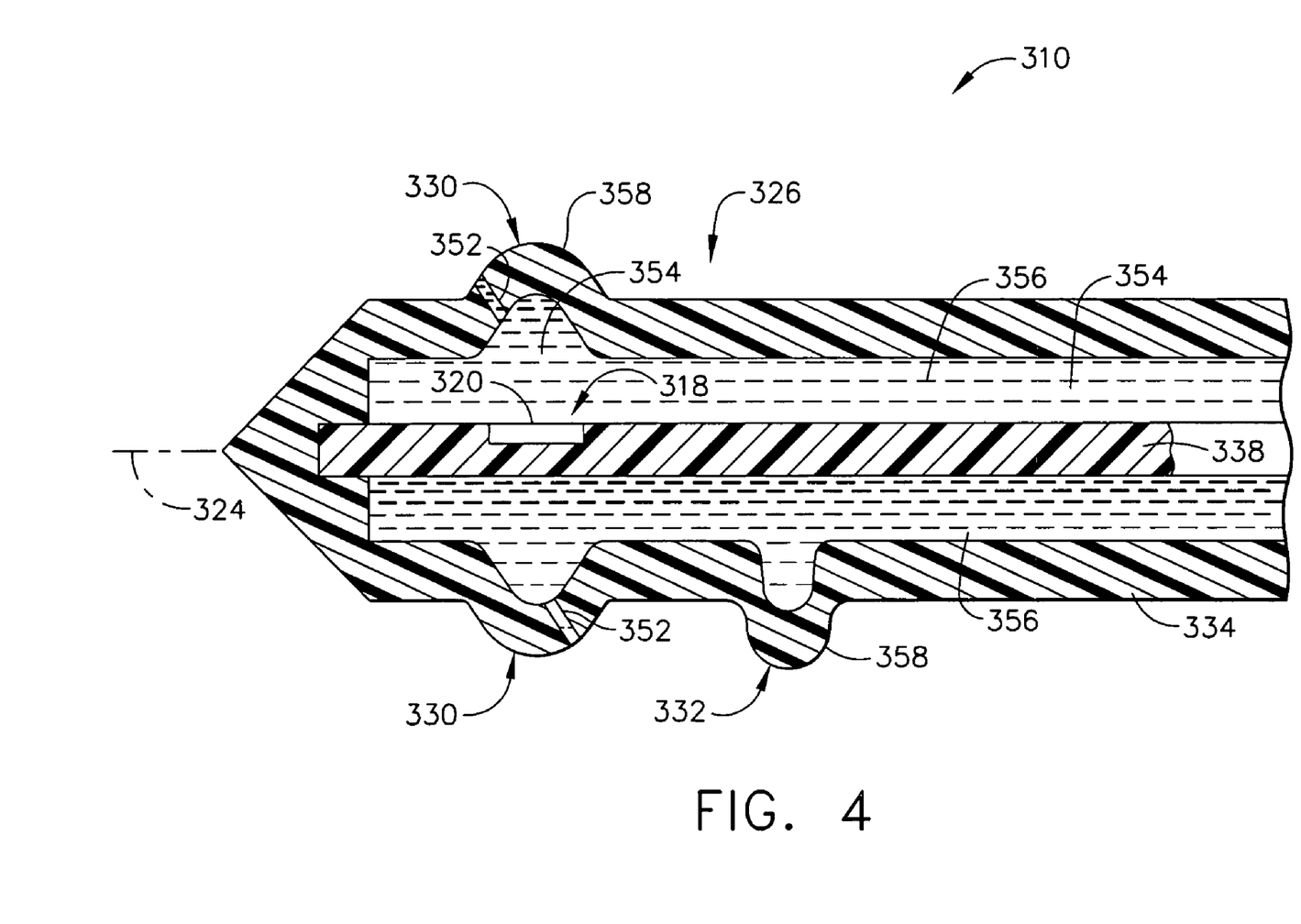
FIG. 4 is a view, as in FIG. 2, but of a third embodiment of an end effector having a medical ultrasound transducer assembly supported by a shaft and having a surrounding sheath, wherein the sheath includes two balloon portions.

A third embodiment of the present invention, shown in FIG. 4, is an ultrasound medical system 310 comprising an ultrasound end effector 326 including a shaft 338, a sheath 334, and a medical ultrasound transducer assembly 318. The medical ultrasound transducer assembly 318 is supported by the shaft 338 and has at least one medical-treatment ultrasound transducer 320. The sheath 334 surrounds the shaft 338. The sheath 334 includes at least one balloon portion 330 and 332 which is expandable against patient tissue to provide at least some stabilization of the ultrasound end effector 326 with respect to patient tissue.

In one example of the embodiment of FIG. 4, the ultrasound end effector 326 is insertable into a patient. In one variation, the ultrasound end effector 326 is an ultrasound interstitial end effector which is interstitially insertable into patient tissue. In other variations, the ultrasound end effector is insertable into a patient in an endoscopic, laparoscopic, and/or open surgical manner. In another example, the ultrasound end effector is disposable on the outside of a patient. Other examples and variations are left to the artisan.

In one construction of the embodiment of FIG. 3, the ultrasound end effector 326 has a longitudinal axis 324, and the at-least-one balloon portion (e.g., 330) acts as an acoustic window and is disposed to longitudinally overlap the at-least-one medical-treatment ultrasound transducer 320. In one variation of this construction, the at-least-one balloon portion (e.g., 330) includes at least one through hole 352. In one modification, the at-least-one balloon portion (e.g., 330) includes a plurality of through holes 352 creating a "weeping" balloon portion, wherein some of the acoustic coupling medium inside the sheath 334 extends and/or flows outside the sheath acoustic window providing improved acoustic coupling between the at-least-one medical-treatment ultrasound transducer 320 and patient tissue.

In one arrangement of the embodiment of FIG. 3, the at-least-one balloon portion (e.g., 330) includes at least one through hole 352 and the ultrasound end effector 326 is adapted to dispense a drug 354 through the at-least-one through hole 352 to patient tissue. In one variation, the drug 354 is carried in a liquid acoustic coupling medium 356, such as water, disposed between the medical ultrasound transducer assembly 318 and the at-least-one balloon portion 330 whose pressure is controlled (such as by a pump in a handpiece operatively connected to the ultrasound end effector) to expand and contract the at-least-one balloon portion 330. In one variation, the drug 354 is at least potentiated (i.e., has its medical effect increased and/or activated) by ultrasound emitted from the at-least-one medical-treatment ultrasound transducer 320.

In the same or another arrangement of the embodiment of FIG. 3, the ultrasound end effector 326 has a longitudinal axis 324, and the at-least-one balloon portion (e.g., 332) is disposed longitudinally apart from the at-least-one medical-treatment ultrasound transducer 320. In one variation of the embodiment of FIG. 3, the at-least-one balloon portion (e.g., 330) is a fully-circumferential balloon portion. In a different variation, the at-least-one balloon portion (e.g., 332) is a blister balloon portion. In one example of the embodiment of FIG. 3, the at-least-one balloon portion 330 and 332 includes an outside surface 358 having a roughness average at least equal to 0.005-inch. In one variation, the outside surface includes ribs. Such surface roughness improves stabilization of the ultrasound end effector 326 with respect to patient tissue when the at-least-one balloon portion 330 and 332 is expanded against the patient tissue.

The embodiments, constructions, implementations, etc. of the embodiments of FIGS. 1-2 and 3 are equally applicable to the embodiment, constructions, implementations, etc. of the embodiment of FIG. 4. In one implementation of the embodiment of FIG. 3, the ultrasound medical system 310 also includes a controller, like the controller of the previously-illustrated and described arrangement of the embodiment of FIGS. 1-2, wherein the controller is operatively connected to the medical ultrasound transducer assembly, wherein the medical ultrasound transducer assembly is a medical-imaging-and-treatment ultrasound transducer assembly, and wherein the controller determines if the at-least-one balloon portion is acoustically coupled to, or acoustically decoupled from, patient tissue from ultrasonically imaging a balloon-tissue area using the medical-imaging-and-treatment ultrasound transducer assembly.

Figure 5:
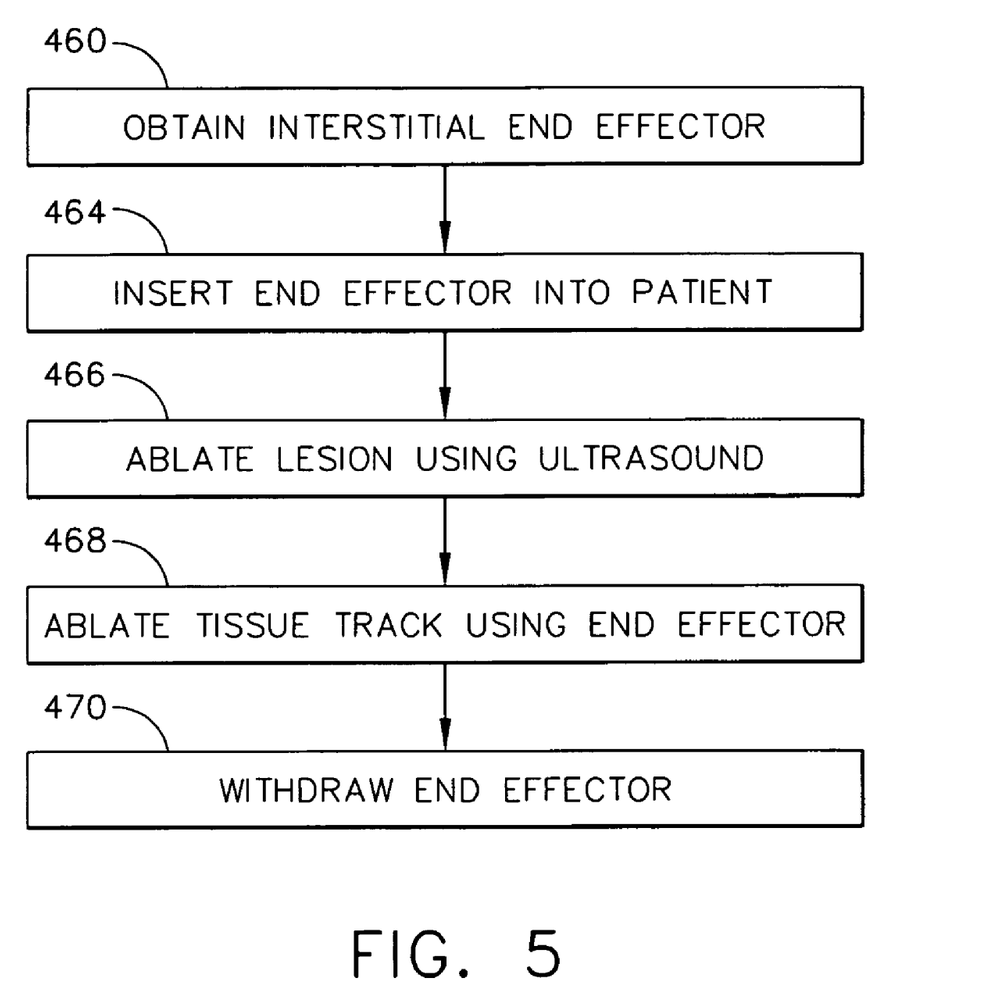
FIG. 5 is a block diagram view of a method of the invention for ultrasonically treating a lesion in a patient.
Figure 6:
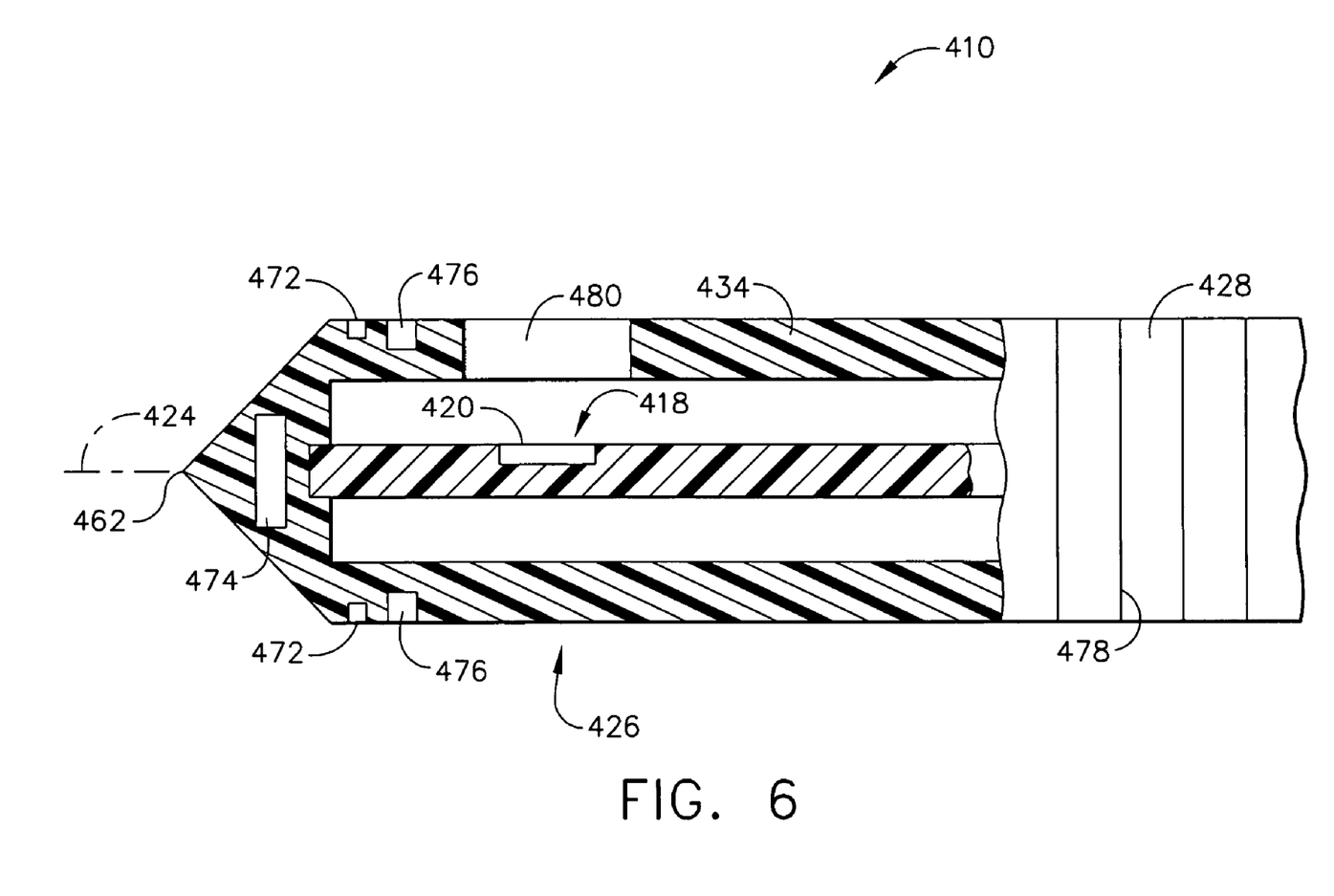
FIG. 6 is a schematic view, partially in cross-section, of a fourth embodiment of an end effector which has a medical-treatment ultrasound transducer and three end-effector-tissue-track ablation devices and which can be used in one employment of the method of FIG. 5.

One method of the invention for ultrasonically treating a lesion in a patient is shown in block diagram form in FIG. 5, and an embodiment of an ultrasound medical system which can be used in performing the method is shown in FIG. 6. The method includes steps a) through e). Step a) is labeled as "Obtain Interstitial End Effector" in block 460 of FIG. 5. Step a) includes obtaining an interstitial end effector 426 including a distal end 462 and including a medical ultrasound transducer assembly 418 having at least one medical-treatment ultrasound transducer 420 and at least one end-effector-tissue-track ablation device 472, 474 and 476; It is noted that the distal end of an interstitial end effector is an end having a tissue-piercing tip. Step b) is labeled as "Insert End Effector Into Patient" in block 464 of FIG. 5. Step b) includes inserting the interstitial end effector 426 into the patient creating a tissue track which is surrounded by patient tissue and which ends at the distal end 462 of the inserted interstitial end effector 426. Step c) is labeled as "Ablate Lesion Using Ultrasound" in block 466 of FIG. 5. Step c) includes ultrasonically ablating the lesion using the at-least-one medical-treatment ultrasound transducer 420. Step d) is labeled as "Ablate Tissue Track Using End Effector" in block 468 of FIG. 5. Step d) includes using the at-least-one end-effector-tissue-track ablation device 472, 474 and 476 to ablate the patient tissue surrounding the tissue track along substantially the entire tissue track. Step e) is labeled as "Withdraw End Effector" in block 470 of FIG. 5. Step e) includes withdrawing the interstitial end effector 426 from the patient.

It is noted that creating a tissue track requires that the interstitial end effector 426 be interstitially inserted into patient tissue. It is also noted that the interstitial end effector 426 can be equipped with a retractable tip shield (not shown) for initial endoscopic or laparoscopic patient entry followed by interstitial insertion into patient tissue.

In one extension of the method of FIG. 5, there is included the step of using the at-least-one end-effector-tissue-track ablation device (e.g., 474) to ablate the patient tissue at the distal end 462 of the inserted interstitial end effector 426.

In one implementation of the method of FIG. 5, the at-least-one end-effector-tissue-track ablation device (e.g., 474) includes a non-ultrasound energy source, and step d) uses the non-ultrasound energy source to ablate the patient tissue surrounding the tissue track. In one variation, the non-ultrasound energy source is chosen from the group consisting of a resistive heat energy source, a hot liquid energy source, a monopolar radio-frequency (RF) energy source, a bipolar radio-frequency (RF) energy source, a capacitive heat energy source, a microwave energy source, and combinations thereof.

In another implementation of the method, the at-least-one end-effector-tissue-track ablation device (e.g., 476) includes a tissue-ablating chemical agent, and step d) uses the tissue-ablating chemical agent to ablate the patient tissue surrounding the tissue track. In one variation, the tissue-ablating chemical agent is chosen from the group consisting of fibrin, alcohol, an acidic fluid, a chemotherapeutic agent, and combinations thereof.

In a further implementation of the method, step d) uses the medical ultrasound transducer assembly 418 to ultrasonically ablate the patient tissue surrounding the tissue track. In one variation, step d) ultrasonically ablates at a higher ultrasound frequency than does step c).

In the same or another extension of the method of FIG. 5, there is included the step of monitoring (such as for acoustic coupling and/or for tissue ablation) the patient tissue surrounding the tissue track during step d). In one variation, the monitoring is chosen from the group consisting of B-mode ultrasonic image monitoring, tissue temperature monitoring, tissue electric impedance, and combinations thereof.

In the same or another extension of the method of FIG. 5, there are included, after step b) and before step c), the step of stabilizing (such as by using a balloon, a tine and/or suction) the interstitial end effector 426 with respect to the patient tissue surrounding the tissue track and, after step c) and before step d), the step of releasing the stabilizing of the interstitial end effector 426 with respect to the patient tissue surrounding the tissue track.

In one application of the method of FIG. 5, step e) includes stepwise withdrawing the interstitial end effector 426 from the patient using a plurality of positional steps, and step d) includes ablating the patient tissue surrounding the tissue track for a predetermined time with the interstitial end effector at each positional step.

A fourth embodiment of the present invention, shown in FIG. 6, is an ultrasound medical system 410 comprising an interstitial end effector 426 which is interstitially insertable into patient tissue, which includes at least one medical-treatment ultrasound transducer 420, and which includes at least one end-effector-tissue-track ablation device 472, 474 and 476.

In one enablement of the embodiment of FIG. 6, the ultrasound medical system 410 includes a controller (such as the controller 142 illustrated in FIG. 1) which is operatively connected to the at-least-one medical-treatment ultrasound transducer 420 to ultrasonically ablate a lesion in patient tissue of the patient and which is operatively connected to the at-least-one end-effector-tissue-track ablation device 472, 474 and 476 to ablate patient tissue surrounding the interstitial end effector 426 during withdrawal of the interstitial end effector 426 from the patient.

In one application of the embodiment of FIG. 6, the at-least-one end-effector-tissue-track ablation device 472, 474, 476 includes a cylindrical ultrasound transducer 472. In the same or a different application, the at-least-one end-effector-tissue-track ablation device and the at-least-one medical-treatment ultrasound transducer are a single rotatable ultrasound transducer (such as ultrasound transducer 420 made rotatable such as in a previously illustrated and described implementation of the embodiment of FIGS. 1-2). Other applications of an end-effector-tissue-track ablation device involving ultrasound are left to the artisan.

In another application of the embodiment of FIG. 6, the at-least-one end-effector-tissue-track ablation device 472, 474 and 476 includes a device 474 which uses a non-ultrasound energy source. In one variation, the non-ultrasound energy source is chosen from the group consisting of a resistive heat energy source, a hot liquid energy source, a monopolar radio-frequency (RF) energy source, a bipolar radio-frequency (RF) energy source, a capacitive heat energy source, a microwave energy source, and combinations thereof.

In a further application of the embodiment of FIG. 6, the at-least-one end-effector-tissue-track ablation device 472, 474 and 476 includes a device 476 which releases a tissue-ablating chemical agent. In one variation, the tissue-ablating chemical agent is chosen from the group consisting of fibrin, alcohol, an acidic fluid, a chemotherapeutic agent, and combinations thereof.

In one construction of the embodiment of FIG. 6, the interstitial end effector 426 has a length and an exterior surface 428 and includes position markings 478 on the exterior surface 428 along at least a portion of its length. Such position markings allow a user to withdraw the interstitial end effector 426 from patient tissue in positional steps while ablating patient tissue surrounding the end-effector tissue track for a predetermined dwell time at each positional step. In the same or a different construction, the interstitial end effector 426 has a longitudinal axis 424 and a distal end 462, and wherein the at-least-one end-effector-tissue-track ablation device 472, 474 and 476 includes an end-effector-tissue-track ablation device (such as 474) which is disposed proximate the distal end 462. It is noted that the distal end of an interstitial end effector is an end having a tissue-piercing tip. In the same or a different construction, the interstitial end effector 426 includes a tissue-ablating component (such as 474) adapted (such as by having a resistive heat energy source) to ablate (such as to thermally ablate) patient tissue longitudinally forward of the distal end 462.

In one variation, the ultrasound interstitial end effector includes a sheath 434 surrounding the medical-treatment ultrasound transducer 120 and having an acoustic window 480. In one modification, the entire sheath acts as an acoustic window. In another modification, the acoustic window is a thinner portion of the sheath. In a further modification, the acoustic window is a separate material(s) from the material(s) of the non-acoustic-window portion(s) of the sheath. Acoustic window component materials are known to those skilled in the art. Other modifications are left to the artisan.

It is noted that the embodiments, constructions, implementations, etc. of the embodiments of FIGS. 1-2, 3 and 4 are equally applicable to the embodiment, constructions, implementations, etc. of the embodiment of FIG. 6.

Several benefits and advantages are obtained from one or more of the embodiments and methods of the invention. In one example, having a non-ultrasound tissue-property-measuring sensor (such as a tissue temperature sensor and/or a tissue electric impedance sensor) allows ultrasound tissue ablation with feedback from the sensor used to evaluate the tissue ablation and/or modify the ultrasound treatment.

While the present invention has been illustrated by a description of several embodiments and methods, it is not the intention of the applicants to restrict or limit the spirit and scope of the appended claims to such detail. Numerous other variations, changes, and substitutions will occur to those skilled in the art without departing from the scope of the invention. For instance, the ultrasound medical system of the invention has application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended claims.

What is claimed is:

1. An ultrasound medical system comprising:
    an ultrasound end effector, wherein the ultrasound end effector includes a sheath having an exterior surface, and wherein the ultrasound end effector is an ultrasound interstitial end effector which is interstitially insertable into patient tissue;
    at least one non-ultrasound tissue-property-measuring sensor, wherein the at-least-one non-ultrasound tissue-property-measuring sensor is attached to the ultrasound interstitial end effector and is fixedly disposed substantially flush with the exterior surface; and
    a medical ultrasound transducer assembly having at least one medical-treatment ultrasound transducer, wherein the medical ultrasound transducer assembly including the medical-treatment ultrasound transducer is surrounded by the sheath;
    wherein the at-least-one non-ultrasound tissue-property-measuring sensor is supported by the ultrasound interstitial end effector and is disposable in contact with patient tissue; and
    wherein the exterior surface includes at least one balloon portion which is expandable and contractible and which is expandable against patient tissue to provide at least some stabilization of the ultrasound interstitial end effector with respect to patient tissue, wherein a first balloon portion surrounds the medical ultrasound transducer assembly and acts as an acoustic window and longitudinally overlaps the medical-treatment ultrasound transducer, and wherein an acoustic coupling medium is disposable between the medical ultrasound transducer assembly and the first balloon portion.

2. The ultrasound medical system of claim 1, wherein the ultrasound interstitial end effector includes a longitudinal axis, wherein the at-least-one non-ultrasound tissue-property-measuring sensor includes a first non-ultrasound tissue-property-measuring sensor and a second non-ultrasound tissue-property-measuring sensor, and wherein the at-least-one medical-treatment ultrasound transducer is disposed longitudinally between the first and second non-ultrasound tissue-property-measuring sensors.

3. The ultrasound medical system of claim 1, wherein the at-least-one non-ultrasound tissue-property-measuring sensor measures tissue temperature.

4. The ultrasound medical system of claim 1, wherein the at-least-one non-ultrasound tissue-property-measuring sensor measures tissue electric impedance.

5. The ultrasound medical system of claim 1, wherein the exterior surface includes a second balloon portion longitudinally spaced apart from the medical ultrasound transducer assembly.

6. The ultrasound medical system of claim 1, also including a handpiece operatively connected to the ultrasound interstitial end effector, wherein the ultrasound interstitial end effector has a longitudinal axis and a shaft, wherein the medical ultrasound transducer assembly is supported by the shaft, and wherein the shaft is rotatable with respect to the handpiece about the longitudinal axis.

7. An ultrasound medical system comprising:
    an ultrasound interstitial end effector, wherein the ultrasound interstitial end effector includes a sheath having an exterior surface;
    at least one non-ultrasound tissue-property-measuring sensor, wherein the at-least-one non-ultrasound tissue-property-measuring sensor is deployable to extend away from the exterior surface into patient tissue to provide at least some stabilization of the ultrasound interstitial end effector with respect to patient tissue and is retrievable to retract back toward the exterior surface; and
    a medical ultrasound transducer assembly having at least one medical-treatment ultrasound transducer, wherein the medical ultrasound transducer assembly including the medical-treatment ultrasound transducer is surrounded by the sheath;
    wherein the at-least-one non-ultrasound tissue-property-measuring sensor is supported by the ultrasound interstitial end effector and is disposable in contact with patient tissue; and
    wherein the exterior surface includes at least one balloon portion which is expandable and contractible and which is expandable against patient tissue to provide at least some stabilization of the ultrasound interstitial end effector with respect to patient tissue, wherein a first balloon portion surrounds the medical ultrasound transducer assembly and acts as an acoustic window and longitudinally overlaps the medical-treatment ultrasound transducer, and wherein an acoustic coupling medium is disposable between the medical ultrasound transducer assembly and the first balloon portion.

8. The ultrasound medical system of claim 7, wherein the at-least-one non-ultrasound tissue-property-measuring sensor is storable inside the exterior surface.

9. The ultrasound medical system of claim 7, wherein the ultrasound interstitial end effector includes a longitudinal axis, wherein the at-least-one non-ultrasound tissue-property-measuring sensor includes a first non-ultrasound tissue-property-measuring sensor and a second non-ultrasound tissue-property-measuring sensor, and wherein the at-least-one medical-treatment ultrasound transducer is disposed longitudinally between the first and second non-ultrasound tissue-property-measuring sensors.

10. The ultrasound medical system of claim 7, wherein the at-least-one non-ultrasound tissue-property-measuring sensor measures tissue temperature.

11. The ultrasound medical system of claim 7, wherein the at-least-one non-ultrasound tissue-property-measuring sensor measures tissue electric impedance.

12. The ultrasound medical system of claim 7, wherein the exterior surface includes a second balloon portion longitudinally spaced apart from the medical ultrasound transducer assembly.

13. The ultrasound medical system of claim 7, also including a handpiece operatively connected to the ultrasound interstitial end effector, wherein the ultrasound end effector has a longitudinal axis and a shaft, wherein the medical ultrasound transducer assembly is supported by the shaft, and wherein the shaft is rotatable with respect to the handpiece about the longitudinal axis.

* * * * *